US009638643B2

(12) United States Patent
De Jong et al.

(10) Patent No.: US 9,638,643 B2
(45) Date of Patent: May 2, 2017

(54) PARTICULATE CONTAMINATION MEASUREMENT METHOD AND APPARATUS (71) Applicants: ASML Netherlands B.V., Veldhoven (NL); TNO, Delft (NL)

(72) Inventors: Antonius Martinus Cornelis Petrus De Jong, Pijnacker (NL); Jacques Cor Johan Van Der Donck, Alphen aan den Rijn (NL)

(73) Assignee: ASML Netherlands B.V., Veldhoven (NL)

(*) Notice: Subject to any disclaimer, the term of this patent is extended or adjusted under 35 U.S.C. 154(b) by 69 days.

(21) Appl. No.: 14/389,075

(22) PCT Filed: Mar. 28, 2013

(86) PCT No.: PCT/EP2013/056794
§ 371 (c)(1),
(2) Date: Sep. 29, 2014

(87) PCT Pub. No.: WO2013/149961
PCT Pub. Date: Oct. 10, 2013

(65) Prior Publication Data
US 2015/0055127 A1 Feb. 26, 2015
Related U.S. Application Data (60) Provisional application No. 61/619,209, filed on Apr. 2, 2012.

(51) Int. Cl.
*G01N 21/00* (2006.01)
*G01N 21/94* (2006.01)
*G03F 7/20* (2006.01)
*G03F 1/82* (2012.01)
*B32B 37/24* (2006.01)
(Continued)

(52) U.S. Cl.
CPC ............ *G01N 21/94* (2013.01); *B32B 37/24* (2013.01); *B32B 38/10* (2013.01); *G01N 21/956* (2013.01);
(Continued)

(58) Field of Classification Search
CPC ...... G01N 21/94; G01N 21/956; G01N 21/47; G01N 2001/028; G01N 2001/2833;
(Continued)

(56) References Cited

U.S. PATENT DOCUMENTS 5,047,649 A 9/1991 Hodgson et al.
6,408,701 B1 6/2002 Fujita
(Continued)

FOREIGN PATENT DOCUMENTS

CN 101256364 A 9/2008
JP 60-159634 A 8/1985
(Continued)

OTHER PUBLICATIONS

International Search Report directed to related International Patent Application No. PCT/EP2013/056794, mailed Jul. 2, 2013; 5 pages.
(Continued)

*Primary Examiner* — Tri T Ton
(74) *Attorney, Agent, or Firm* — Sterne, Kessler, Goldstein & Fox P.L.L.C.

(57) ABSTRACT

A particulate contamination measurement method and apparatus are discussed. The method, for example, comprises pressing a measurement surface (5) of a polyurethane elastomer (2) against a surface (7) to be measured, removing the polyurethane elastomer from the surface without leaving residues, then using an optical apparatus (11) to detect particles (8) which have been removed by the polyurethane elastomer from the surface and which have become attached to the polyurethane elastomer.

19 Claims, 4 Drawing Sheets (51) Int. Cl.
  *B32B 38/10* (2006.01)
  *G01N 21/956* (2006.01)
  *G01N 21/47* (2006.01)
  *G01N 1/02* (2006.01)
  *G01N 1/28* (2006.01)

(52) U.S. Cl.
  CPC .............. *G03F 1/82* (2013.01); *G03F 7/7085* (2013.01); *G03F 7/70908* (2013.01); *B32B 2037/243* (2013.01); *G01N 21/47* (2013.01); *G01N 2001/028* (2013.01); *G01N 2001/2833* (2013.01); *G01N 2201/06113* (2013.01); *G01N 2201/105* (2013.01)

(58) Field of Classification Search
  CPC .... G01N 2201/06113; G01N 2201/105; B32B 37/24; B32B 38/10; B32B 2037/243; G03F 1/82; G03F 7/7085; G03F 7/70908
  See application file for complete search history.

(56) References Cited

U.S. PATENT DOCUMENTS

| | | |
|---|---|---|
| 6,449,035 B1 | 9/2002 | Batchelder |
| 2003/0043419 A1* | 3/2003 | Brown ............... G03G 21/0035 358/443 |
| 2009/0014030 A1 | 1/2009 | De Jong et al. |
| 2011/0159440 A1 | 6/2011 | Nakajima et al. |

FOREIGN PATENT DOCUMENTS

| | | |
|---|---|---|
| JP | 07-020034 A | 1/1995 |
| JP | 2005-052784 A | 3/2005 |
| JP | 2005-521886 A | 7/2005 |
| JP | 2006-119477 A | 5/2006 |
| JP | 2008-300605 A | 12/2008 |
| JP | 2009-016838 A | 1/2009 |
| JP | 2009-036809 A | 2/2009 |
| JP | 2010-230646 A | 10/2010 |

OTHER PUBLICATIONS

International Preliminary Report on Patentability and Written Opinion of the International Searching Authority directed to related International Patent Application No. PCT/EP2013/056794, issued Oct. 7, 2014; 8 pages.

\* cited by examiner

PARTICULATE CONTAMINATION MEASUREMENT METHOD AND APPARATUS

CROSS-REFERENCE TO RELATED APPLICATIONS

This application claims the benefit of U.S. provisional application 61/619,209, which was filed on 2 Apr. 2012, and which is incorporated herein in its entirety by reference.

FIELD OF THE INVENTION

The present invention relates to a particulate contamination measurement apparatus, a sampler for acquiring removable particulate contamination from a solid surface, a method that is suitable for measuring particulate contamination of a surface, and a method for manufacturing a sampler for acquiring removable particulate contamination from a solid surface, for example a surface of a component of a lithographic apparatus.

BACKGROUND ART

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

Lithography is widely recognized as one of the key steps in the manufacture of ICs and other devices and/or structures. However, as the dimensions of features made using lithography become smaller, lithography is becoming a more critical factor for enabling miniature IC or other devices and/or structures to be manufactured.

A theoretical estimate of the limits of pattern printing can be given by the Rayleigh criterion for resolution as shown in equation (1):

$$CD = k_1 * \frac{\lambda}{NA} \quad (1)$$

where $\lambda$ is the wavelength of the radiation used, NA is the numerical aperture of the projection system used to print the pattern, $k_1$ is a process dependent adjustment factor, also called the Rayleigh constant, and CD is the feature size (or critical dimension) of the printed feature. It follows from equation (1) that reduction of the minimum printable size of features can be obtained in three ways: by shortening the exposure wavelength $\lambda$, by increasing the numerical aperture NA or by decreasing the value of $k_1$.

In order to shorten the exposure wavelength and, thus, reduce the minimum printable size, it has been proposed to use an extreme ultraviolet (EUV) radiation source. EUV radiation is electromagnetic radiation having a wavelength within the range of 5-20 nm, for example within the range of 13-14 nm. It has further been proposed that EUV radiation with a wavelength of less than 10 nm could be used, for example within the range of 5-10 nm such as 6.7 nm or 6.8 nm. Such radiation is termed extreme ultraviolet radiation or soft x-ray radiation. Possible sources include, for example, laser-produced plasma sources, discharge plasma sources, or sources based on synchrotron radiation provided by an electron storage ring.

EUV radiation may be produced using a plasma. A radiation system for producing EUV radiation may include a laser for exciting a fuel to provide the plasma, and a source collector apparatus for containing the plasma. The plasma may be created, for example, by directing a laser beam at a fuel, such as particles of a suitable material (e.g., tin), or a stream of a suitable gas or vapor, such as Xe gas or Li vapor. The resulting plasma emits output radiation, e.g., EUV radiation, which is collected using a radiation collector. The radiation collector may be a mirrored normal incidence radiation collector, which receives the radiation and focuses the radiation into a beam. The source collector apparatus may include an enclosing structure or chamber arranged to provide a vacuum environment to support the plasma. Such a radiation system is typically termed a laser produced plasma (LPP) source.

If contamination were to be present within an EUV lithographic apparatus then that contamination could introduce errors into patterns projected by the EUV lithographic apparatus onto substrates. For example, a contamination particle may become attached to a patterned area of a patterning device in the EUV lithographic apparatus, thereby obscuring part of the patterned area and introducing an error into the projected pattern. It is therefore desirable to minimise contamination, particularly particulate contamination, in the EUV lithographic apparatus. One way in which this may be done is to measure particulate contamination of surfaces of components that are to be used to assemble an EUV lithographic apparatus. A component may for example be rejected and/or cleaned if the measured particulate contamination of its surfaces is too high.

A known principle of contact cleaning surfaces by removing particles from a given surface makes use of tacky materials assembled in devices such as floor mats, contact rollers or manual rollers. Various tacky materials used in such particle removing devices include polyurethanes, latex, or soft rubbers.

The use of such tacky materials is also known in particle detection methods being used for transferring the particles onto the surface of the tacky materials and analyzing the surface with microscopy. The tape lift method is for example an analytical method that use tacky materials like latex tapes.

However, such tacky materials standardly contain adhesives, chemicals, release agents or polymer components that can be released. Such materials may leave minimal residues at contact, however for EUV applications even such low residue level may be unacceptable. US 06449035 B1 describes for example materials which are said to leave no residues. However the polymer materials disclosed therein are materials which still may leave to some extent (mono) layers of silicones on the contacted surface. Although only detectable with advanced surface analyses like XPS, even such minor amount of residues can have detrimental effects when they are present in a EUV lithography scanner, an EUV radiation source or other apparatus. This is because even minor amounts of residue may influence the contamination buildup on optics, thereby changing their output, or have influence on the wetting characteristic in coating processes.

Most of the tacky materials typically used in contact cleaning or in the particle detection methods leave residues such as (mono)layers of organic materials, silicone or refractory components, which are not acceptable for the high cleanliness requirements in EUV lithography.

SUMMARY

It is desirable to provide a novel particulate contamination measurement apparatus and method that complies with the above mentioned high cleanliness requirements providing a simple manner to collect removable particles in a controlled way.

According to a first aspect of the invention there is provided a particulate contamination measurement apparatus comprising a layer of polyurethane elastomer carried by a carrier, the carrier being configured to allow a measurement surface of the polyurethane elastomer to be pressed against a surface to be measured and then removed.

The measurement surface of the polyurethane elastomer may be ultra-clean.

The polyurethane elastomer may have a hardness that is below about 80 Shore A.

The polyurethane elastomer may have a hardness that is greater than about 20 Shore OO, such as greater than 20 Shore A.

The measurement surface of the polyurethane elastomer may have a roughness that is equal to or less than about 1 micron Ra.

The carrier may be a substrate that is provided with a hole, the measurement surface of the polyurethane elastomer being accessible through the hole.

The substrate may be flexible.

The carrier may have the shape and size of a credit card blank.

A flexible material may be provided on an opposite side of the polyurethane elastomer from the hole.

The carrier may be a probe. The polyurethane elastomer may be provided on an end of the probe.

According to a second aspect of the invention there is provided a particulate contamination measurement apparatus comprising a flexible material that is more flexible than a metal surface such that a measurement surface of the flexible material will establish a greater contact area with a contamination particle than a contact area between the contamination particle and the metal surface, the flexible material being sufficiently strong that a residue will not be transferred from the measurement surface to the metal surface, the measurement surface being ultra clean. The flexible material that is more flexible than a metal surface may be self-adhesive.

The metal surface may be a surface of a metal structure such as an aluminum or steel structure. The metal surface may be a metal surface of a component that may form part of an EUV lithographic apparatus.

The measurement apparatus according to the second aspect of the invention may incorporate one or more features of the measurement apparatus according to the first aspect of the invention.

According to a third aspect of the invention there is provided a particulate contamination measurement apparatus, comprising: a material that is more flexible than a solid surface, such that a measurement surface of the material will establish a greater contact area with a contamination particle than a contact area between the contamination particle and the solid surface, wherein the material is sufficiently strong so that a residue will not be transferred from the measurement surface to the solid surface, and wherein the measurement surface is ultra clean.

According to a fourth aspect of the invention there is provided a sampler for acquiring removable particulate contamination from a solid surface comprising: a carrier and a flexible material layer coupled to the carrier, the flexible material layer having an inner surface and an opposing outer surface, wherein the carrier is arranged to allow peeling of the flexible material layer from the solid surface, wherein the outer surface is a particle-collecting surface adapted to transfer removable particulate contamination from the solid surface to the outer surface upon contact, and wherein the flexible material layer leaves less than 2E-12 mbar/1 sec.*$cm^2$ organic materials having a weight average molecular weight in a range from 44 to 100 g/mol onto the solid surface after contacting said solid surface, as determined by residual gas analysis.

The flexible material layer may leave less than 1.5E-13 mbar/sec.*$cm^2$ organic materials having a weight average molecular weight in a range from 101 to 200 g/mol onto the solid surface after contacting said solid surface, as determined by residual gas analysis.

The flexible material layer may leave less than 0.1 atomic % of Pb, Zn, Sn, In, and Si as residue onto the solid surface and in the corresponding environment, after contacting said solid surface, as determined by XPS.

The flexible material layer may leave less than 0.5 atomic percent of other elements than Pb, Zn, Sn, In, and Si as residue onto the solid surface and in the corresponding environment, after contacting said solid surface, as determined by XPS.

The flexible material layer may be a polyurethane elastomer layer having a hardness in a range from 20 to 80 Shore A.

The sampler may be obtainable by a process comprising the following steps:
a) Preparing the polyurethane elastomer on a clean substrate under controlled conditions to obtain an ultra-clean polyurethane elastomer layer;
b) Peeling off the ultra-clean polyurethane elastomer layer from the clean substrate; and
c) couple it to the carrier to form a sampler. At least part of one or both of the sampler surface(s) may be covered with a removable protective foil to protect the ultra-clean polyurethane elastomer layer from contamination.

The outer surface of the polyurethane elastomer layer, being the particle-collecting surface, may have a roughness of about 10 times less than the mean average particle size.

According to a fifth aspect of the invention, there is provided a particulate contamination measurement method comprising pressing a measurement surface of a polyurethane elastomer against a surface to be measured, removing the polyurethane elastomer from the surface, then using an optical apparatus to detect particles that have been removed by the polyurethane elastomer from the surface and that have become attached to the polyurethane elastomer.

The polyurethane elastomer may be self-adhesive.

The polyurethane elastomer may have a hardness that is below about 80 Shore A.

The polyurethane elastomer may have a hardness that is greater than about 20 Shore OO. The shore values were determined according to the ASTM D2240 method.

The polyurethane elastomer may be carried by a carrier.

The measurement surface of the polyurethane elastomer may have a roughness that is equal to or less than about 1 micron Ra.

The carrier may be a substrate that is provided with a hole, the measurement surface of the polyurethane elastomer being accessible through the hole.

The substrate may be flexible.

The carrier may be a probe. The polyurethane elastomer may be provided on an end of the probe.

It may be the case that no residue is transferred from the polyurethane elastomer to the surface being measured.

The flexible material, such as the polyurethane elastomer, may be arranged to be self-adhesive to the carrier.

According to a sixth aspect of the invention there is provided a particulate contamination measurement method comprising pressing a flexible material onto a metal surface to be measured, the flexible material being more soft than the metal surface such that it establishes a greater contact area with a contamination particle than a contact area between the contamination particle and the metal surface, the contamination particle therefore becoming attached to the flexible material, the flexible material being sufficiently strong that it does not leave a residue on the metal surface, wherein the method further comprises removing the flexible material from the metal surface, then using an optical apparatus to detect contamination particles that have been attached to the flexible material. By "strong" herein is meant that the cohesive forces of the polymer structure of the flexible material are far larger than the adhesion forces between polymer and surface which are acting on the polymer during removal of the polymer.

The metal surface may be a surface of a metal structure such as an aluminum or steel structure. The metal surface may be a metal surface of a component that may form part of an EUV lithographic apparatus.

The measurement method according to the sixth aspect of the invention may incorporate one or more features of the measurement method according to the fifth aspect of the invention.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in that corresponding reference symbols indicate corresponding parts, and in which.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Figure 1:
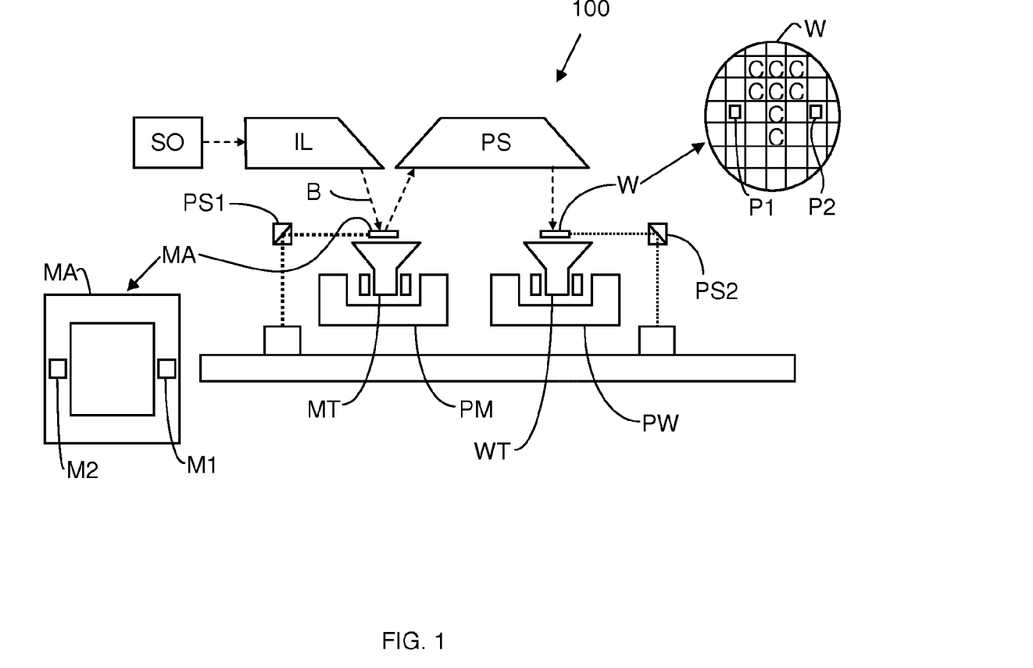
FIG. 1 depicts a lithographic apparatus.

FIG. 1 schematically depicts a lithographic apparatus 100 including a source collector apparatus SO. The apparatus comprises:

an illumination system (illuminator) IL configured to condition a radiation beam B (e.g., EUV radiation).

a support structure (e.g., a mask table) MT constructed to support a patterning device (e.g., a mask or a reticle) MA and connected to a first positioner PM configured to accurately position the patterning device;

a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure MT holds the patterning device MA in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system.

The term "patterning device" should be broadly interpreted as referring to any device that can be used to impart a radiation beam with a pattern in its cross-section such as to create a pattern in a target portion of the substrate. The pattern imparted to the radiation beam may correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam that is reflected by the mirror matrix.

The projection system, like the illumination system, may include various types of optical components, such as refractive, reflective, magnetic, electromagnetic, electrostatic or other types of optical components, or any combination thereof, as appropriate for the exposure radiation being used, or for other factors such as the use of a vacuum. It may be desired to use a vacuum for EUV radiation since other gases may absorb too much radiation. A vacuum environment may therefore be provided to the whole beam path with the aid of a vacuum wall and vacuum pumps.

As here depicted, the apparatus is of a reflective type (e.g., employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

Referring to FIG. 1, the illuminator IL receives an extreme ultra violet radiation beam from the source collector apparatus SO. Methods to produce EUV light include, but are not necessarily limited to, converting a material into a plasma state that has at least one element, e.g., xenon, lithium or tin, with one or more emission lines in the EUV range. In one such method, often termed laser produced plasma ("LPP") the required plasma can be produced by irradiating a fuel, such as a droplet, stream or cluster of material having the required line-emitting element, with a laser beam. The source collector apparatus SO may be part of an EUV radiation system including a laser, not shown in FIG. 1, for providing the laser beam exciting the fuel. The resulting plasma emits output radiation, e.g., EUV radiation, which is collected using a radiation collector, disposed in the source collector apparatus. The laser and the source collector apparatus may be separate entities, for example when a $CO_2$ laser is used to provide the laser beam for fuel excitation.

In such cases, the laser is not considered to form part of the lithographic apparatus and the radiation beam is passed from the laser to the source collector apparatus with the aid of a beam delivery system comprising, for example, suitable directing mirrors and/or a beam expander. In other cases the source may be an integral part of the source collector apparatus, for example when the source is a discharge produced plasma EUV generator, often termed as a DPP source.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as facetted field and pupil mirror devices. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. After being reflected from the patterning device (e.g., mask) MA, the radiation beam B passes through the projection system PS, which focuses the beam onto a target portion C of the substrate W. With the aid of the second positioner PW and position sensor PS2 (e.g., an interferometric device, linear encoder or capacitive sensor), the substrate table WT can be moved accurately, e.g., so as to position different target portions C in the path of the radiation beam B. Similarly, the first positioner PM and another position sensor PS1 can be used to accurately position the patterning device (e.g., mask) MA with respect to the path of the radiation beam B. Patterning device (e.g., mask) MA and substrate W may be aligned using mask alignment marks M1, M2 and substrate alignment marks P1, P2.

The depicted apparatus could be used in at least one of the following modes:

1. In step mode, the support structure (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed.
2. In scan mode, the support structure (e.g., mask table) MT and the substrate table WT are scanned synchronously while a pattern imparted to the radiation beam is projected onto a target portion C (i.e., a single dynamic exposure). The velocity and direction of the substrate table WT relative to the support structure (e.g., mask table) MT may be determined by the (de-)magnification and image reversal characteristics of the projection system PS.
3. In another mode, the support structure (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
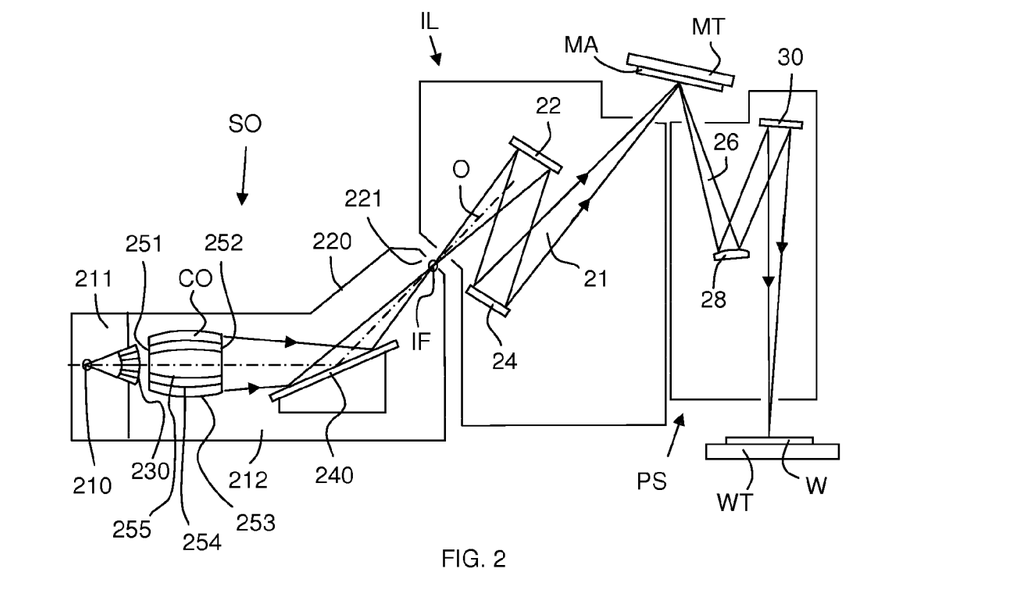
FIG. 2 is a more detailed view of the lithographic apparatus.

FIG. 2 shows the apparatus 100 in more detail, including the source collector apparatus SO, the illumination system IL, and the projection system PS. The source collector apparatus SO is constructed and arranged such that a vacuum environment can be maintained in an enclosing structure 220 of the source collector apparatus SO. An EUV radiation emitting plasma 210 may be formed by a discharge produced plasma source. EUV radiation may be produced by a gas or vapor, for example Xe gas, Li vapor or Sn vapor in which the very hot plasma 210 is created to emit radiation in the EUV range of the electromagnetic spectrum. The very hot plasma 210 is created by, for example, an electrical discharge causing an at least partially ionized plasma. Partial pressures of, for example, 10 Pa of Xe, Li, Sn vapor or any other suitable gas or vapor may be required for efficient generation of the radiation. A plasma of excited tin (Sn) may be provided to produce EUV radiation.

The radiation emitted by the hot plasma 210 is passed from a source chamber 211 into a collector chamber 212 via an optional gas barrier or contaminant trap 230 (in some cases also referred to as contaminant barrier or foil trap), which is positioned in or behind an opening in source chamber 211. The contaminant trap 230 may include a channel structure. Contamination trap 230 may also include a gas barrier or a combination of a gas barrier and a channel structure. The contaminant trap or contaminant barrier 230 further indicated herein at least includes a channel structure, as known in the art.

The collector chamber 212 may include a radiation collector CO that may be a so-called grazing incidence collector. Radiation collector CO has upstream radiation collector side 251 and a downstream radiation collector side 252. Radiation that traverses collector CO can be reflected off a grating spectral filter 240 to be focused in a virtual source point IF. The virtual source point IF is commonly referred to as the intermediate focus, and the source collector apparatus is arranged such that the intermediate focus IF is located at or near an opening 221 in the enclosing structure 220. The virtual source point IF is an image of the radiation emitting plasma 210.

Subsequently the radiation traverses the illumination system IL, which may include a facetted field mirror device 22 and a facetted pupil mirror device 24 arranged to provide a desired angular distribution of the radiation beam 21, at the patterning device MA, as well as a desired uniformity of radiation intensity at the patterning device MA. Upon reflection of the beam of radiation 21 at the patterning device MA, held by the support structure MT, a patterned beam 26 is formed and the patterned beam 26 is imaged by the projection system PS via reflective elements 28, 30 onto a substrate W held by the wafer stage or substrate table WT.

More elements than shown may generally be present in illumination optics unit IL and projection system PS. The grating spectral filter 240 may optionally be present, depending upon the type of lithographic apparatus. Further, there may be more mirrors present than those shown in the Figures, for example there may be 1-6 additional reflective elements present in the projection system PS than shown in FIG. 2.

Collector optic CO, as illustrated in FIG. 2, is depicted as a nested collector with grazing incidence reflectors 253, 254 and 255, just as an example of a collector (or collector mirror). The grazing incidence reflectors 253, 254 and 255 are disposed axially symmetric around an optical axis O and a collector optic CO of this type is preferably used in combination with a discharge produced plasma source, often called a DPP source.

Figure 3:
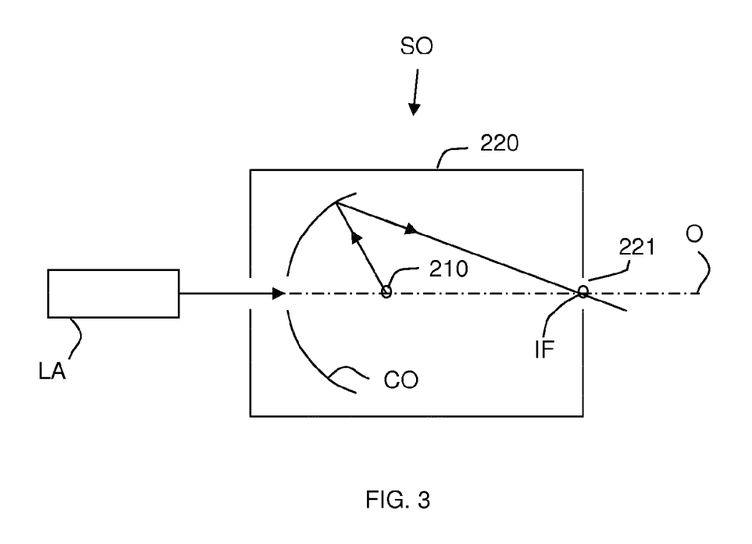
FIG. 3 is a more detailed view of a source collector apparatus of the lithographic apparatus of FIGS. 1 and 2.

Alternatively, the source collector apparatus SO may be part of an LPP radiation system as shown in FIG. 3. A laser LA is arranged to deposit laser energy into a fuel, such as xenon (Xe), tin (Sn) or lithium (Li), creating the highly ionized plasma 210 with electron temperatures of several 10's of eV. The energetic radiation generated during de-excitation and recombination of these ions is emitted from the plasma, collected by a near normal incidence collector optic CO and focused onto the opening 221 in the enclosing structure 220.

Contamination from an EUV radiation source, such as those described in FIGS. 2 and 3, or contamination which is present within the EUV lithographic apparatus 100 may introduce errors into patterns projected by the apparatus onto the substrate W. For example, a contamination particle may become attached to the patterning device MA and may obscure part of the pattern provided on the patterning device. Where this is the case, the pattern projected onto the substrate W will include an error. The error may be sufficiently large that an integrated device formed on the substrate W does not function correctly. Contamination at other locations in the lithographic apparatus may also give rise to errors in the pattern projected onto the substrate W. It may therefore be desirable to minimise or reduce contamination, particularly particulate contamination, in the EUV lithographic apparatus.

One way in which particulate contamination may be minimised or reduced is by ensuring that components, which are used to assemble the EUV lithographic apparatus, are sufficiently clean (e.g., have surfaces with particulate contamination that is below a threshold level). Particulate contamination of a surface may be measured using the apparatus shown schematically in FIG. 4. The particulate contamination may have a (sub)micron size.

Figure 4:
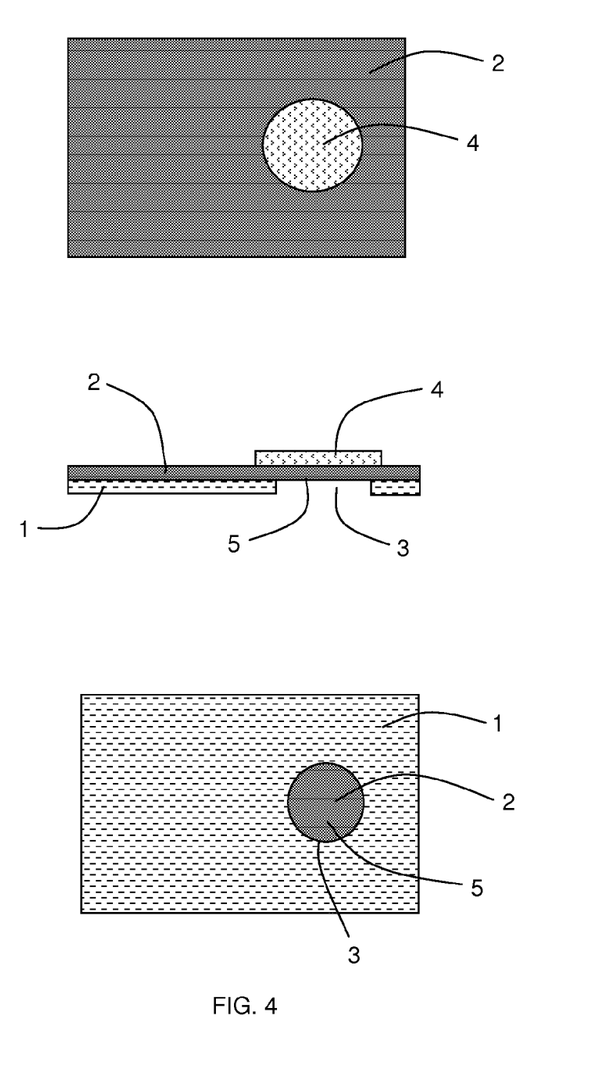
FIG. 4 is a schematic illustration of a particulate contamination measurement apparatus according to an embodiment of the invention.

FIG. 4 shows, going from top to bottom, an embodiment of the particulate contamination measurement apparatus according to the invention viewed from above, viewed in cross-section, and viewed from below. Herein by "above" or "top" is meant the part (i.e surface or side) of the particulate contamination measurement apparatus where a pressing tool is contacted with a layer of a flexible material, such as a polyurethane elastomer. Herein by "below" or "bottom" it is meant the opposite part of the apparatus where the flexible material, such as the polyurethane elastomer, (measurement) surface inspected for particulate contamination is visible. The apparatus comprises a carrier 1 upon which a layer of polyurethane elastomer 2 is provided. The carrier 1 includes a hole 3 (i.e. an opening) that is configured such that the polyurethane elastomer layer 2 is visible through the hole when viewing the apparatus from below. A disk made from a foil 4 is provided on a top surface of the polyurethane elastomer layer 2 (i.e. on the surface of the polyurethane elastomer which is contacted by the pressing tool), the foil disk 4 being aligned (or substantially aligned) with the hole 3. The foil disk 4 may have a diameter that is greater than the diameter of the hole 3. The foil disk 4 is flexible and provides a contact surface onto which pressure may be applied when using the apparatus (as described further below). The bottom surface of the polyurethane elastomer layer 2 that is visible through the hole 3 acts as a measurement surface 5 to which contamination particles become attached when the apparatus is used (i.e. is contacted with a solid surface). The measurement surface 5 may, for example, have a diameter of around 16 mm or an area of about 30-35 mm$^2$ where using a 50× magnification for inspecting the particulate contamination. Alternatively, the measurement surface 5 may have any other suitable diameter or area, for example an area matching the measurement field area of the optical instrument used for detecting the particulate contamination.

The carrier 1 may for example be formed from plastic. The carrier 1 may for example be a credit card blank (i.e., a piece of plastic that is dimensioned to form a credit card but that has yet not been processed to become a credit card). Any suitable substrate (e.g., a flexible substrate) may be used as a carrier.

The foil 4 is preferably a non-sticky cover foil which provides a surface on the polyurethane elastomer layer 2 onto which a pressing tool may press (as described further below) such that neither the polyurethane elastomer layer 2, nor foil 4 will adhere to the pressing tool. Although the illustrated foil 4 is a disk, the foil may have any suitable shape. For instance the foil 4 may cover only a part or the full available top surface of the polyurethane elastomer layer 2. Similarly, although the hole 3 is circular, the hole may have any suitable shape. Furthermore, the foil does not need being aligned with the hole 3 as long as the surface of the polyurethane elastomer to be pressed is covered at least in a region where the pressing tool may be applied for collecting the particulate contamination. The foil 4 may for example be a metal foil such as aluminium foil. Any suitable flexible material may be used that provides a surface onto which a pressing tool may press without adhering to the foil 4.

Furthermore, the bottom surface of the carrier 1 may be temporarily protected with another covering foil (not shown in FIG. 4) that is removed before the apparatus needs to be used in order to protect the entire apparatus and especially the measurement surface 5 of the polyurethane elastomer layer 2 from any kind of contamination.

Figure 5:
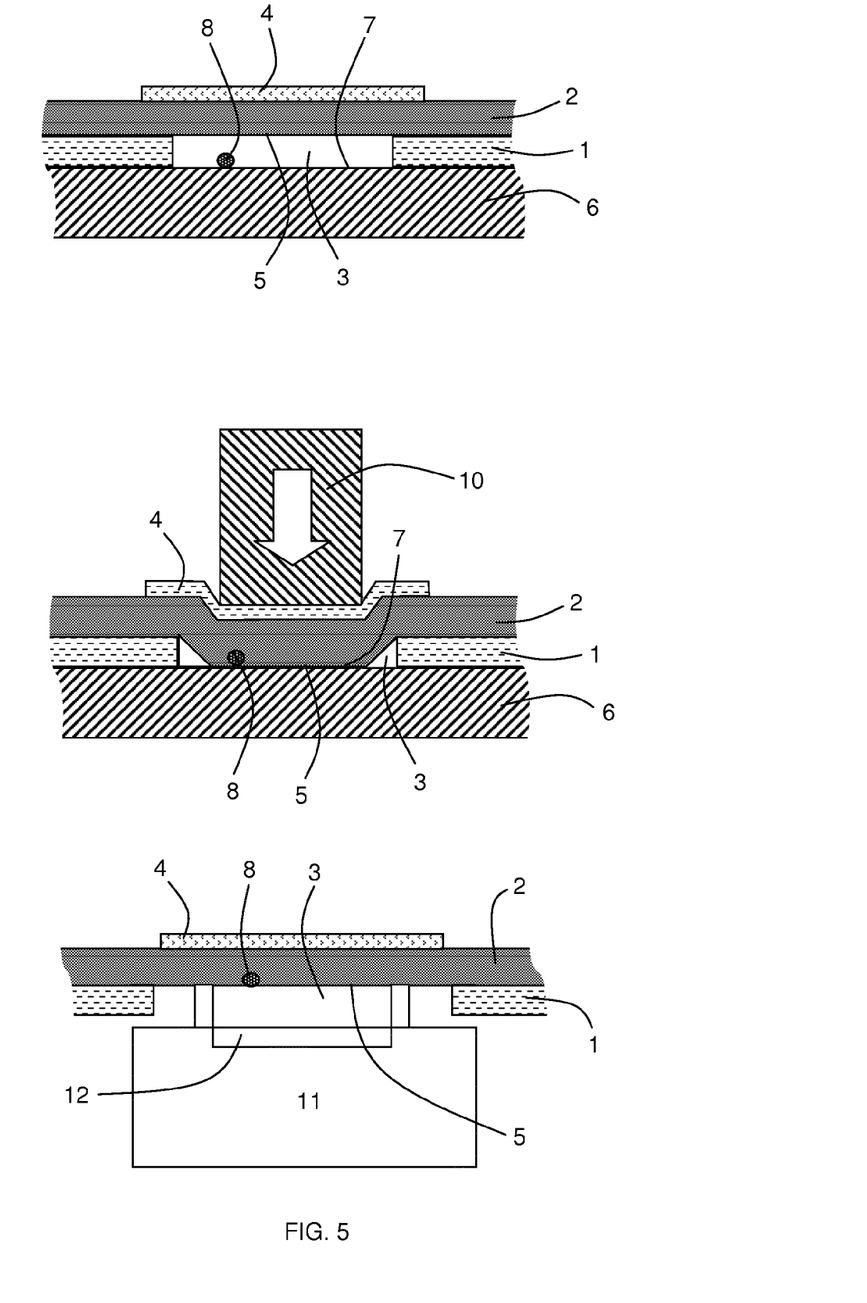
FIG. 5 is a schematic illustration of a particulate contamination measurement method according to an embodiment of the invention.

Operation of the apparatus shown in FIG. 4 is illustrated schematically in FIG. 5. Referring first to the top of FIG. 5, the particulate contamination of a surface 7 of a component 6 is to be measured. The particulate contamination may be of any nature, such as metal, oxide, ceramics, organic material etc. The surface 7 may be a solid surface of any suitable material such as metal, glass, ceramics or plastics. The component 6 may for example be a component of an EUV lithographic apparatus (e.g., a metal structure that forms part of the EUV lithographic apparatus). A contamination particle 8 is present on the surface 7 of the component. The contamination particle is oversized in FIG. 5 for ease of illustration. The measurement apparatus has been put on the surface 7 of the component 6, the carrier 1 resting upon the surface 7 of the component. The polyurethane elastomer layer 2 is not in contact with the surface 7 but instead is held above the surface 7 by the carrier 1.

Referring to the middle part of FIG. 5, a pressing tool 10 presses downwards on the flexible foil disk 4 (as indicated schematically by the arrow). The pressing tool 10 presses the measurement surface 5 of the polyurethane elastomer layer 2 against the surface 7 of the component 6. The pressing tool 10 pushes the polyurethane elastomer layer 2 into the hole 3 in the carrier 1, thereby bringing the measurement surface 5 of the polyurethane elastomer layer into contact with the surface 7 of the component 6. The contamination particle 8 becomes thus attached to the polyurethane elastomer layer 2.

The pressing tool 10 may press with a pressure greater than or equal to 20 gram/cm$^2$. A pressure greater than or equal to about 20 gram/cm$^2$ may be sufficient for contamination particles to become attached to the measurement surface 5. A pressure of around 200 gram/cm$^2$ may for example be used. A typical pressure may be below 10 N/cm$^2$.

In an embodiment, the pressing tool 10 may be configurable to press the measurement surface 5 of the polyurethane elastomer 2 against the component surface 7 with a pressure in the range of about 50-1000 gram/cm$^2$. Where this is the case, a pressure towards the bottom end of that range may be sufficient for contamination particles to become attached to the measurement surface 5.

In an embodiment, the measurement surface 5 may be manually pressed against the component surface, for example by a user pressing onto the foil 4 with a finger or thumb.

The pressing tool 10 may be removed from the flexible foil disk 4 after for example one second or less. This allows the polyurethane elastomer 2 to be released from the surface 7 of the component 6. Van der Waals forces exerted between the measurement surface 5 of the polyurethane elastomer 2 and the surface 7 of the component 6 may be such that the polyurethane elastomer remains attached to the surface after the pressing tool 10 has been removed. The polyurethane elastomer 2 may be released from the surface 7 by manually lifting the carrier 1 such that the polyurethane elastomer is drawn away from the surface. Alternatively, the resilience of the polyurethane elastomer 2 may be such that the polyurethane elastomer pulls away from the surface 7 and returns to the configuration shown in the upper part of FIG. 5.

Once the polyurethane elastomer 2 has been released from the surface 7 of the component 6, the measurement apparatus may then be transferred to an optical apparatus 11 (e.g., a PartSens sensor, available from ACP GmbH Oelbronn-Duerrn of Germany). The measurement surface 5 may rest upon a perimeter of an imaging array 12 of the optical apparatus 11, as is schematically shown (the imaging array may measure approximately 5 mm×6 mm). The optical apparatus 11 illuminates the measurement surface 5 of the polyurethane elastomer 2. Light that is scattered from the attached particle 8 is detected by the imaging array 12 of the optical apparatus 11. The optical apparatus 11 provides an image in which particles can be identified. The number of particles that are detected by the optical apparatus 11 provides an indication of the particulate contamination on the surface 7 of the component 6.

Any suitable optical apparatus may be used to allow particulate contamination on the measurement surface 5 of the polyurethane elastomer layer to be measured (e.g., any suitable imaging optical apparatus).

The apparatus and method of the invention is advantageous because the polyurethane elastomer 2 does not leave (detectable) residue on the surface 7 of the component 6. By "residue" herein is meant (undesired) contamination elements such as particles or organic contamination. Such contamination include for example organic materials, silicone, refractory components, particles of any material and combinations thereof.

Such residue is undesirable within the EUV lithographic apparatus because the residue will contaminate the vacuum established in the EUV lithographic apparatus during operation of the lithographic apparatus. The polyurethane elastomer is sufficiently soft that it can be pressed against the component surface 7 such that contamination particles 8 become attached to the polyurethane elastomer and remain attached to the polyurethane elastomer when the polyurethane elastomer is removed from the component surface 7 (i.e., the contamination particles are removed from the component surface). This attachment of the contamination particles 8 is achieved without a glue or other adhesive (which are otherwise typically used in contact cleaning and contamination inspection devices to attach the tacky material to a support surface of the device) that would be likely to leave a residue on the surface 7 of the component 6.

The polyurethane elastomer 2 and the particulate contamination measurement apparatus may also be sufficiently flexible to follow any 3D surface shape. The particulate contamination measurement apparatus may be sufficiently flexible to be effective on rough surfaces 7 having Ra≤5 micron.

The polyurethane elastomer 2 may be sufficiently resilient that it has no memory of the shape of a surface 7 against which it has been pressed. That is, if the polyurethane elastomer layer 2 is pressed against a patterned surface 7, then the polyurethane elastomer layer 2 may be distorted around that patterned surface 7 but will then return to its original flat shape after it has been removed from the patterned (rough) surface (i.e. it will not show no false positives and will retain its original shape being easily inspectable under the microscope). For example, the polyurethane elastomer layer 2 may return to the original shape within less than 10 seconds, preferably within less than 2 seconds. This is advantageous because in some circumstances distortion of the measurement surface 5 of the polyurethane elastomer layer 2 could add noise to a particulate contamination measurement.

The polyurethane elastomer layer 2 may be sufficiently resilient that it will not be damaged if it is pressed onto a rough component surface with a pressure of for example up to 1000 gram/cm$^2$ (for some materials such a threshold pressure may be even higher). This is advantageous because in some circumstances damage of the measurement surface 5 of the polyurethane elastomer 2 could add noise to a particulate contamination measurement.

The attachment of a contamination particle 8 to the measurement surface 5 of the polyurethane elastomer layer 2 occurs mainly due to van der Waals forces. A spherical contamination particle (e.g., metal particle with a diameter of a few microns) will have a limited contact area to a metal component surface. For example, around 10% of the spherical particle may be in contact with the metal surface. The polyurethane elastomer layer 2 is sufficiently soft that it deforms around the contamination particle, and therefore establishes a contact area with the contamination particle 8 that is greater than the contact area between the contamination particle 8 and the metal component surface 7 (e.g., a contact area of greater than 10%). As a result, the van der Waals forces exerted by the polyurethane elastomer 2 on the contamination particle 8 are greater than the van der Waals forces exerted by the metal component surface 7 on the contamination particle. When the polyurethane elastomer 2 is removed from the metal component surface 7 the contamination particle 8 is therefore retained by the polyurethane elastomer 2 and is removed from the metal component surface 7 (the contamination particle 8 adheres to the polyurethane elastomer 2 and remains attached to the polyurethane elastomer 2).

The composition of the polyurethane elastomer 2 may be selected in order to obtain a desired softness by tuning the degree of crosslinking and the average polymer chain length of the polyurethane elastomer, such that van der Waals forces between the measurement surface of the polyurethane elastomer and contamination particles are sufficiently strong for the contamination particles 8 to adhere to the polyurethane elastomer 2 when it is removed from the metal component surface 7. The manner in which constituents of the polyurethane elastomer 2 may be selected to provide a desired softness will be known to those skilled in the art.

The composition of the polyurethane elastomer may also be selected in order to obtain a desired hardness such that the polyurethane elastomer returns to its previous shape after it has been distorted by being pressed against a patterned surface. The manner in which constituents of the polyurethane elastomer may be selected to provide a desired hardness will be known to those skilled in the art.

The polyurethane elastomer 2 may for example have a hardness that is below about 80 Shore A and may for example have a hardness that is equal to or less than about 70 Shore A. Such Shore values provides sufficient flexibility to the polyurethane elastomer. The harder the polyurethane elastomer is, the more difficult it is for the polyurethane elastomer to deform sufficiently to provide an accurate particulate contamination measurement for a rough component surface 7. Above 80 Shore A the polyurethane elastomer may be for instance already too hard for properly contacting (3D) surfaces. For example, polyurethane elastomer 2 with a hardness that is equal to or less than about 70 Shore A may be used when performing a particulate contamination measurement for a component surface 7 having a roughness greater than about 3 Ra microns.

The polyurethane elastomer 2 may for example have a hardness that is greater than about 20 Shore OO, and may for example have a hardness that is equal to or greater than about 30 Shore OO. The softer the polyurethane elastomer 2, the greater the likelihood that a residue will be left behind on the component surface 7 following a particulate contamination measurement.

In an embodiment the polyurethane elastomer has a hardness in a range from 20 to 80 Shore A. Such a shore value was found to provide an application area with a relatively low residue risk of contamination with residues.

In another embodiment the polyurethane elastomer has a hardness in a range from 38 to 75 Shore A. In yet another embodiment the polyurethane elastomer has a hardness in a range from 40 to 70 Shore A. Such Shore values have been found to ensure a sufficient crosslinking level and a sufficient molecular chain length to have a lower risk of contamination with residues.

A shore value in the range of less than 20 Shore A and more than 20 Shore 00 provided a softer polyurethane elastomer which had a reasonable level of tackiness (since tackiness increases with decreasing shore) however it presented a higher risk for contamination due to insufficient crosslinking. A Shore value below 20 Shore 00 was generally not applicable since the level of residues was found too high.

All Shore values mentioned herein were determined using the ASTM D2240 method. This method allows for a measurement of the initial hardness, or the indentation hardness. ASTM D2240 refers to several rubber hardness measurement scales (A, B, C, D, DO, O, OO and M) and uses several types of indenters depending on the hardness range, such as a flat 35° angle cone point for determining Shore A values and a 3/32" spherical indenter for Shore OO values. The skilled person knows which hardness scale and which corresponding indenter need to be used in a specific hardness range.

The above referenced Shore (A and OO) values may depend to some extent on the thickness of the polyurethane elastomer layer 2. When choosing the thickness of the polyurethane elastomer layer 2 it should be taken into account that too thin layers may be more easily damaged, whereas for too thick layers may leads to decrease in flexibility of deforming the polyurethane elastomer layer 2. The ASTM D2240 method for determining Shore value requires test specimens of the polyurethane elastomer layer 2 of about 6.4 mm (¼ in) thickness. It is possible to pile several test specimens to achieve the 6.4 mm thickness, although one test specimen is preferred.

The polyurethane elastomer layer 2 may have any suitable thickness. The polyurethane elastomer layer 2 may be sufficiently thick that it does not break during normal use of the measurement apparatus. The polyurethane elastomer layer 2 may for example have a thickness of less than about 50 mm, and may for example have a thickness of less than 10 mm. The polyurethane elastomer may for example have a thickness greater than 0.1 mm, and may for example have a thickness greater than 1 mm. The thickness of the polyurethane elastomer layer 2 may be for instance in a range from 1 to 10 mm.

In addition to an appropriate hardness as defined by the Shore level, also the manufacturing of the polyurethane elastomer is preferably done under controlled conditions to minimize any risk of contamination.

Before using the polyurethane elastomer 2 to measure particulate contamination on the surface 7 of a component 6 that will be used in an EUV lithographic apparatus, the polyurethane elastomer 2 is preferably tested experimentally to determine whether it fulfills the residue requirements. Performing such test provides the appropriate check whether the process steps in the polyurethane elastomer and the apparatus manufacturing were performed under controlled conditions without adding any cross contamination to the polyurethane elastomer (such as no silicones, additives, release agents, other cross contamination) in order to reach the final high cleanliness level of the polyurethane elastomer that leaves a minimal amount and preferably no residues.

The measurement surface 5 of the polyurethane elastomer layer 2 may be ultra-clean. The term "ultra-clean" may be interpreted as meaning that there is less than 15 particles with a diameter greater than 2 microns per square centimeter of the measurement surface 5 of the polyurethane elastomer 2 before contacting with surface 7. In a vacuum environment typical for EUV lithography the requirements on residues left by the measurement surface 5 after contacting surface 7 may be even higher. In an embodiment, there may be less than 1 particle with a diameter greater than 0.1 micron per square centimeter on the surface of the surface 7 before contacting with the measurement surface 5 of the polyurethane elastomer 2. In another embodiment, also no molecular residues are left by the measurement surface 5 (i.e. by polyurethane elastomer layer 2) on surface 7 after contacting them, as determined with XPS and rest gas analyses. Such level of surface cleanliness also after contact is advantageous in order to minimize contamination of the analyzed surface 7 in an EUV lithographic environment (or other alike environments where vacuum and cleanliness are of critical importance) with the particulate contamination measurement apparatus itself.

In a vacuum environment such as typically for EUV lithography or other applications requiring high level of cleanliness various upper limits of allowed amount of residues may be used depending on the application field. Below are listed such embodiments which may be used in EUV lithography related products.

Preferably less than 1 particle/cm$^2$ are provided to the surface and in the corresponding environment after pressing (e.g. contacting) the polyurethane elastomer onto surface 7 for a time up to 10 seconds (sec.).

Preferably less than 0.1 atomic % of Pb, Zn, Sn, In, and Si is left as residue on surface 7 and in the corresponding environment, after pressing the polyurethane elastomer onto surface 7, as determined by XPS. Preferably less than 0.5 atomic percent of other elements than Pb, Zn, Sn, In, and Si is left as residue on surface 7 and in the corresponding environment, after pressing the polyurethane elastomer onto surface 7, as determined by XPS.

In an EUV environment also it may be advantageous to avoid outgassing in the vacuumed system to avoid contamination of for example the optics or the patterning device. By outgassing herein is meant the mass that is released from surface 7 under vacuum determined as a number of molecules/per time*cm$^2$.

In an embodiment less than 2E-10 mbar/1 sec.*cm$^2$ water is released from surface 7 under vacuum after pressing the polyurethane elastomer onto surface 7, as determined by residual gas analysis.

In an embodiment less than 2E-12 mbar/1 sec.*cm$^2$ organic materials having a molecular weight in a range from 44 to 100 g/mol is released from surface 7 under vacuum after pressing the polyurethane elastomer onto surface 7, as determined by residual gas analysis.

In an embodiment less than 1.5E-13 mbar/sec.*cm$^2$ organic materials having a molecular weight in a range from 101 to 200 g/mol is released from surface 7 under vacuum after pressing the polyurethane elastomer onto surface 7, as determined by residual gas analysis.

The EUV required ultra-clean property as described above for the polyurethane elastomer 2 (and especially for the measurement surface 5) may be achieved by manufacturing the polyurethane elastomer and the corresponding particulate contamination measurement apparatus in a controlled environment free of contamination sources. The recipients and other processing apparatus/devices (such as molds, mixing devices, filters, cover foils etc) and the materials (for instance monomers or other constituents of the polyurethane elastomer) to be processed may for example be cleaned before use. By "cleaned" herein is meant that preferably their surfaces do not contain any particle contamination and are dry. The monomers used to manufacture the polyurethane elastomer are preferably free of micron sized particles, are degassed and dry, in order to avoid any air bubble formation during the curing step of the polyurethane elastomer (i.e. during crosslinking of the polyurethane constituents to form a polymer network). The polymer may be processed in a clean room particle iso class 7 or even cleaner environment.

The mixing ratio and of monomers, the reaction process temperatures (such as in a range from 20 to 60° C.) and other reaction parameters are chosen by the one skilled in the art such that all constituents are completely reacted and that no monomers or short chain molecules are left. In an embodiment no extra additives (fillers, stabilizers, drying agents etc) are added that can decrease the cohesion forces inside the polyurethane elastomer polymer matrix. The end polymer product which is then used in the form of a polyurethane elastomer layer 2 is a relatively strong, partially crosslinked polyurethane elastomer polymer with medium too long polymer chains.

To protect the cleanliness of the polymer surface, in an embodiment the polyurethane elastomer layer 2 may be manufactured with no use of a release agent (such as silicone) in order to minimize the risk of contamination of the surface 7 at contact. Production may be manual or automatised, with the polyurethane elastomer being produced on a (preferably clean) polished surface (e.g., having for example a roughness Ra less than about 0.1 micron) such as a silicon wafer, a glass plate, a polished metal mold or an ultra-clean carrier or foil. In yet another embodiment a part of the production process of the polymer may contain a final cleaning steps of the polymer surface with ultrasonic cleaning in an ultra-pure alcohol and a final soft baking steps at 80-100 C in a (vacuum) oven. The top surface layer may be protected with an cover foil which is free of silicones or release agents. The cover foil may be mounted on both sides of the foil and can be removed on the front side when the material is used for the particle measurement.

After the polyurethane elastomer layer has been fabricated it may be peeled off after more than 10 hour from the surface (e.g., manually), using enough force to overcome a self-adhesive connection between the polyurethane elastomer and the surface. Since the surface upon which the polyurethane elastomer is made is smooth (e.g., roughness less than about 0.1 microns Ra) the measurement surface of the polyurethane elastomer layer will also be smooth (e.g., with a similar roughness). The smooth surface may provide a more accurate particulate contamination measurement than a rough surface, as is explained further below.

In an embodiment, the polyurethane elastomer layer 2 may have less than about 0.1% heavy metals on its surface, as determined with XPS. In an embodiment, the polyurethane elastomer layer 2 may have substantially no defects on the measurement surface 5. In an embodiment, the polyurethane elastomer layer 2 may have less than a (sub)monolayer of silicone present on the measurement surface 5 and more preferably no silicones or other refractory components on the measurement surface 5 as determined by XPS and with rest gas analyses (RGA) of the contacted surface 7. Preferably no particles and organic contamination, including refractory components, are left on the component surface 7 after contacting it with the polyurethane elastomer 2.

The measurement apparatus may be disposable; the measurement apparatus being discarded after a particulate contamination measurement of a component surface has been performed.

The polyurethane elastomer layer 2 may have a surface that is sufficiently flat that a contamination particle present on the surface may be detected without significant background noise. For example if it is desired to be able to detect contamination particles having a diameter as small as 10 microns, the surface roughness of the polyurethane elastomer may be equal to or less than 1 micron Ra (the roughness may for example be average roughness expressed as Ra). If it is desirable to be able to detect contamination particles having a diameter as small as 1 micron, the surface roughness of the polyurethane elastomer may be less than about 0.1 micron Ra. In general, the polyurethane elastomer may have a surface roughness that is less than the diameter of contamination particles that are to be detected, for example the surface roughness of the polyurethane elastomer may be a factor of 10 less than the diameter of the contamination particles to be detected. The polyurethane elastomer may be used to detect for example sub-micron sized particles (the measurement surface of the polyurethane elastomer being provided with an appropriate flatness as described above). The sub-micron sized particles may have mean average diameter of ≥100 nm and the polyurethane elastomer may have an ultra-smooth measurement surface 5 having Ra≤10 nm such that the smaller particles may also be detected with a digital microscope such as Keyence VHX 1000.

The polyurethane elastomer has a tackiness such that is able to transfer particles of different types, shapes and sizes from the component surface 7 to the measurement surface 5 with an efficiency of ≥90%. Typically particles having mean average diameter ≥2 micron may be transferred with ≥90% efficiency and even with ≥95% efficiency.

The polyurethane elastomer 2 may be self-adhesive. That is, the measurement surface 5 of the polyurethane elastomer layer may adhere to the component surface 7 once it has been pressed against the component surface. The adhesiveness of the polyurethane elastomer may be sufficiently low that the polyurethane elastomer 2 can be removed from the component surface by (manually) peeling it away from the component surface. Also, the adhesiveness of the polyurethane elastomer may be sufficiently high that the polyurethane elastomer 2 will retain adhesion to the carrier 1 or to the foil 4 during or after being pressed to contact surface 7.

The peel strength of the polyurethane elastomer 2 peeled off from the component surface 7 can be chosen to match a specific application; generally it may be chosen between 1 and 50 gram/cm.

In an embodiment, the measurement surface 5 may be pressed multiple times onto a component surface 7. The measurement surface may be pressed multiple times onto the same part of the component surface, or onto different parts of the component surface.

The particulate contamination measurement apparatus and the corresponding measurement method may be used to measure particulate contamination over a wide range of different levels of particulate contamination. The method is suitable for relatively low particle concentration, for example ≤1 particles/cm$^2$ of 2 micron mean average diameter and larger per surface area, such that they are individually visible by the measurement instrument. For example, the method and the particulate contamination measurement apparatus according to the invention may be used at a low particle concentration of 0.1 particles/cm$^2$ up to a high particle concentration of 10,000 particles/cm$^2$ (i.e., a particle concentration in the range of about 0.1-10,000 particles per cm$^2$ for particles ≥2 micron mean average diameter). Experiments performed using the measurement method have generated the results indicated below in Table 1.

TABLE 1

| Analysed sample | Particles (>=2 micron) #/cm2 |
|---|---|
| Ultra clean PET foil | 0.38 |
| Wipe cleaned PVC (Ra < 0.1) | 7.2 |
| Climafoil (polyester side) | 7.8 |
| Ultrasonic cleaned stainless steel (Ra = 2.4) | 15 |
| Climafoil (polyethylene side) | 211 |
| Aluminum foil (rough side) | 670 |
| Ultrasonic cleaned cleaned glass blasted stainless steel | 3100 |
| Tip scew driver | 10000 |

In Table 1 PET foil refers to film formed using polyethylene terephthalate, and US cleaned SS refers to ultrasonically cleaned stainless steel. Climafoil refers to foil that is available under that name for example from Floter Verpackungs-Service GmbH of Schwieberdingen, Germany.

In Table 2 below some maximum contamination levels as required for component surfaces 7 for use in EUV lithography related products are given. The values are measured with XPS and are in atomic %.

TABLE 2

| Maximum residue levels | XPS atomic % |
|---|---|
| Pb | 0.1 |
| Zn | 0.1 |
| Sn | 0.1 |
| In | 0.1 |
| Si | 0.1 |
| other elements | 0.5 |

The maximum outgassing level may be measured using a residual gas analysis (RGA) procedure, which is a Semicon procedure for materials that are used in ultra-clean vacuum (for EUV lithography). Such analytical service is delivered for example by Metron Technology cleaning center. The water outgassing, the low molecular weight organic materials (molecular weight 44-100) and high molecular weight organic materials (molecular weight 101-200) were determined using the residual gas analysis method. The component surface 7 contacted by the measurement surface 5 preferably should have an outgassing level below the requirements for EUV lithography application as listed below:

| | |
|---|---|
| water | 2E−10 mbar/l sec * cm$^2$ |
| organic materials (MW 44-100) | 2E−12 mbar/l sec. * cm$^2$ |
| organic materials (MW 101-200) | 1.5E−13 mbar/l sec. * cm$^2$. |

In order to reach the low residue levels required for EUV clean environments the polyurethane elastomer was processes under controlled conditions. The choice of polyurethane base chemicals and the curing conditions were done in a way that the polyurethane elastomer polymer reached a high degree of cross linking with medium and long polymer chains, which also increased the shore value but also minimized the short non-crosslinked chain polymers molecules that have a higher potential to leave residues. In addition the use of additives (like releasing agents, fillers, drying agents)

during production and curing was completely avoided to minimize the risk of cross contaminations. For other high tech applications (such as aerospace products, OLED, OPV, etc.) the above mentioned residue requirements might be sufficient but further verification for the specific application area may be needed.

A sample of an ultra-clean polyurethane elastomer GP-PMC-12PU from Gelpak, having a hardness value of 35 Shore A was used to experimentally prove that the above cleanliness requirements for EUV lithography were fulfilled, as shown by both XPS tests and RGA tests. Other similar polyurethane elastomers having even higher Shore A values, such as 45 Shore A (or more) may also be commercially available.

X-ray photoelectron spectroscopy (XPS) was used to confirm that residue was not transferred from the measurement surface 5 of the polyurethane elastomer layer 2 to a metal surface 7. The metal surface for this experiment was ultra clean Ruthenium (used because it contains no trace Si in contrast with most aluminium or stainless steel). The measurement surface 5 of the polyurethane elastomer layer 2 was brought into contact with surface 7. The amount of residues on the contacted surface 7 of the ultra-clean sample was below the detection level of the XPS (0.1 atomic %) thereby fulfilling the requirements listed in table 2. The measurement surface 5 of the polyurethane elastomer layer 2 was brought into contact with the Ruthenium surface multiple times, and X-ray photoelectron spectroscopy was then used to monitor for the presence of refractory components (e.g., silicones) or other unwanted residues. No such components or residues were detectable.

Also a residual gas analysis (RGA) measurement was performed, which is a standard procedure for semiconductor materials that are used in ultra clean vacuum (such as for EUV lithography). Ultrasonic cleaned and vacuum baked stainless steel plates (each having an areas of 1600 cm$^2$) were contacted multiple times (1000 presses/m$^2$) with a particulate contamination measurement apparatus comprising GP-PMC-12PU polyurethane elastomer layer 2. The contacted plates did not show a relevant increase of the RGA outgassing compared to clean reference plates. The measured outgassing was in fact on the detection level of the used rest gas equipment: for water 3E-11 mbar*l/sec*cm$^2$, for organics with a molecular weight in a range of 44 to 100 g/mol it was 3E-13 mbar*l/sec*cm$^2$, and for organic materials with a molecular weight in a range of 101 to 200 g/mol it was 4E-14 mbar*l/sec*cm$^2$. All the measured contamination values were therefore well below mentioned requirements for EUV lithography application.

Experiments have been used to verify that contamination particles that are attached to the measurement surface 5 (and thus removed from the component surface 7) are retained by the measurement surface. The measurement surface was pressed against a component surface 7 eight times (a different area on the component surface being used each time), and the number of contamination particles present on the measurement surface was measured each time. The number of contamination particles was observed to increase linearly, thereby confirming that contamination particles are retained by the measurement surface. This experiment was performed using polystyrene latex (PSL) particles with 10 micron diameter and using particles with about 3 micron diameter, in both instances using a wafer surface and using a stainless steel surface.

The efficiency with which that contamination particles attach to the polyurethane elastomer layer has been experimentally measured by using a PartSens sensor to measure the particulate contamination of a silicon wafer before and after application of the measurement surface to the silicon wafer. It was observed that substantially all of the contamination particles that were initially present on the silicon wafer were removed by the measurement surface of the polyurethane elastomer layer.

In an embodiment, the polyurethane elastomer layer 2 is not glued to the carrier 1, in order to avoid the possibility that glue passes to the measurement surface 5 and is then transferred to the component surface 7. Since the polyurethane elastomer layer 2 is located on top of the carrier 1 in use (as shown in FIG. 5), it is unlikely that the polyurethane elastomer layer 2 will become detached from the carrier when the carrier 1 is raised from the component surface 7 (even if the polyurethane elastomer layer 2 would be insufficiently self-adhesive to the carrier 1).

The carrier 1 may be made from any suitable material. The carrier 1 may be formed from a flexible material, the flexibility allowing the carrier to be more easily removed from the component surface 7 without damaging the measurement surface 5 than would be the case if the carrier were rigid and to minimize the risk of contact wear. The carrier 1 may for example be formed from a flexible polymer such as polyethylene or PVC.

In the embodiment illustrated above the polyurethane elastomer layer 2 lies above the hole 3 until the pressing tool 10 presses against it. However, in an embodiment the polyurethane elastomer layer 2 may extend into the hole 3 without pressure being applied to the polyurethane elastomer layer by the pressing tool. In an embodiment, the polyurethane elastomer layer 2 may fill or substantially fill the hole 3 without pressure being applied to the polyurethane elastomer layer by the pressing tool. Pressure may still be applied by the pressing tool 10 during a particulate contamination measurement. Removal of the carrier 1 from the component surface 7 may be easier in embodiments in which the polyurethane elastomer layer 2 does not extend into the hole 3 because in these embodiments the resilience of the polyurethane elastomer will tend to draw the polyurethane elastomer away from the component surface.

In another embodiment, instead of attaching the polyurethane elastomer layer 2 to a carrier 1 as illustrated, the polyurethane elastomer may be attached to the end of a probe (the probe acting as a carrier for the polyurethane elastomer). The probe may have any flat or 3D shape. For example, polyurethane elastomer may be attached to the end of a probe that is attached to the bottom of the pressing tool 10 shown in FIG. 5. Where this is the case, the pressing tool 10 is used to press the probe and polyurethane elastomer onto the component surface 7. The probe may for example be a metal mold to which the polyurethane elastomer is fixed, or may have any other suitable arrangement. An advantage of this arrangement is that there is no contact between a carrier and the surface of the component being measured. The polyurethane elastomer may also be in the form of a tape.

In yet another embodiment, the polyurethane elastomer may be provided in the form of a rotatably mounted cylinder (e.g., as a roller), which may be rolled over a component surface to be measured. This may increase the area for which a particulate contamination measurement may be performed (a larger area can be covered more easily). It may allow detection of lower levels of particulate contamination (sampling a larger area allows more particles to become attached to the polyurethane elastomer).

In another embodiment, the carrier 1 may be the (flexible) foil 4 provided on the top surface of the polyurethane elastomer for being pressed with a pressing tool 10. In such case the polyurethane elastomer may be a self-adhesive polymer which adheres stronger to the foil 4 than to a solid surface to be contacted for being inspected. In such way the polyurethane elastomer may still be peeled off from the solid surface without being peeled off from the flexible foil.

The particulate contamination measurement apparatus according to the invention requires an ultra-clean surface with no adhesives or release agents and a sufficiently cross-linked (medium to long) polymer chains that does not show relevant residues after contacting the surface.

The polyurethane elastomer layer may for example be formed from the polyurethane elastomer that is used to make a Grippy Pad mobile phone carrier, available from Amazon as ASIN product number B00365050M. The polyurethane elastomer layer may for example be formed from the polyurethane elastomer that is used to make a GekkoDot, available from Amazon as ASIN product number BOO2MGIJIU. In an embodiment according to the invention the polyurethane elastomer is prepared from Gelpak GP-PMC 12PU with 35 Shore A value.

In all instances the polyurethane elastomer may be cleaned before it is used to perform a particulate contamination measurement. The cleaning may comprise ultrasonic cleaning in ultra-pure isopropanol. The cleaning may further comprise subsequently soft baking the polyurethane elastomer in a clean vacuum stove (e.g., for about 24 hours at about 80 degrees Celsius).

The polyurethane elastomer may for example be formed using isocyanate product code MPG-023 and polyalcohol product code PNC-153 from Northstar Polymers LLC of Minneapolis, USA, together with appropriate catalysts, cross-linkers, extenders (e.g., 1,4 butanediol, amines), additives, modifiers and mold release (suitable examples of which will be apparent to those skilled in the art).

In an alternative embodiment, an evidence lifting foil (as used by law enforcement organisations) may be used instead of the polyurethane elastomer. The evidence lifting foil may for example be ESLA film available from WA Products (UK) Ltd as product number B26214. Where the context allows, the evidence lifting foil may have properties described above in the context of polyurethane elastomer.

The polyurethane elastomer and the evidence lifting foil are both examples of a material that is more flexible than a metal surface such that a measurement surface of the material will establish a greater contact area with a contamination particle than a contact area between the contamination particle and the metal surface, the material being sufficiently strong that a residue will not be transferred from the measurement surface to the metal surface, the measurement surface being ultra-clean. Suitable materials other than polyurethane elastomer and the evidence lifting foil may be used. In this context the metal surface may be considered to be a solid metal surface (e.g., the surface of a component that may form part of an EUV lithographic apparatus, such as an aluminum or steel structure). Any of the suitable material other than the polyurethane elastomer and the evidence lifting foil may be self-adhesive.

The particulate contamination measurement method described above in particular for an polyurethane elastomer layer 2 may be considered to be an example of a more general particulate contamination measurement method comprising pressing a (flexible) material onto a metal surface to be measured, the material being more soft than the metal surface such that it establishes a greater contact area with a contamination particle than a contact area between the contamination particle and the metal surface, the contamination particle therefore becoming attached to the material, the material being sufficiently strong that it does not leave a residue on the metal surface, wherein the method further comprises removing the material from the metal surface, then using an optical apparatus to detect contamination particles that have been attached to the material.

The particulate contamination analysis apparatus provides (especially due to the apparatus compact shape and/or the flexible material properties) a fast and handy way of collecting and detecting particles. Analyzing surfaces may take less than about 1 minute and provides repeatable and reliable result.

In an embodiment the polyurethane elastomer may be black or may be sufficiently dark colored that metal contamination particles (e.g., aluminium particles) appear as light areas (due to scattered light) on a dark background when illumination is directed towards the measurement surface 5 of the polyurethane elastomer layer 2. This may be considered to be an example of dark field illumination. This detection method may partially or fully exclude the influence of surface structure of the polyurethane elastomer on particle detection. Dark field illumination may be used combination with a transparent or translucent polyurethane elastomer layer 2, for example if the foil 4 (or other flexible material) is black or dark such that it is not reflective.

In an alternative embodiment, the polyurethane elastomer may be transparent or translucent, with radiation being directed through the polyurethane elastomer layer 2 from an opposite surface to the measurement surface 5. Where this is done, contamination particles (e.g., metal particles) are seen as dark areas on a bright background. This may be considered to be an example of bright field illumination. A potential disadvantage of this embodiment is that damage of the measurement surface or minor defects in the measurement surface could cause dark areas to appear in the polyurethane elastomer, thereby contributing noise to the particulate contamination measurement.

Although the invention has been described in the context of EUV lithographic apparatus components, the invention may be used for other applications (including for example non-EUV lithographic apparatus components, and components of other apparatus). Example of such other applications may be in coating processes, CVD processes, gluing processes, OLED's, OPV, aerospace products, (electron) optics and optic instruments, flat panel devices and display manufacturing, analytical equipment, data storage manufacturing, fluid filter inspection, clean rooms, pharmaceutical manufacturing and handling, precision mechanical manufacturing and health care industries.

In an embodiments the apparatus according to the invention may be a sampler for acquiring removable particulate contamination from a solid surface 7, for example for the purpose of cleaning a surface 7 from particulate contamination. The sampler may be used for the purpose of cleaning surfaces for example by single or multiple pressing to a (solid) surface 7, without further inspection. The sample may for instance comprise a carrier 1 and a flexible material layer 2 coupled to the carrier 1 in a similar construction as in FIG. 4, the flexible material layer having an inner surface and an opposing outer surface. The carrier 1 may be arranged to allow peeling of the flexible material layer 2 from the solid surface 7. The outer surface of the flexible material layer may be a particle-collecting surface adapted to transfer removable particulate contamination from the solid surface to the outer surface upon contact, such that the flexible polymer sheet leaves less than 2E-12 mbar/l sec.*$cm^2$ organic materials having a weight average molecular weight in a range from 44 to 100 g/mol onto the solid surface after contacting said solid surface, as determined by residual gas analysis. In an embodiment the flexible polymer sheet also leaves less than 1.5E-13 mbar/sec.*cm$^2$ organic materials having a weight average molecular weight in a range from 101 to 200 g/mol onto the solid surface after contacting said solid surface, as determined by residual gas analysis. The flexible polymer sheet preferably has a hardness in a range from 20 to 80 Shore A, as determined with ASTM D2240 method. One or more (or all) of the parameters and properties defined above for the particulate contamination measurement apparatus, in particular comprising a layer of polyurethane elastomer with the above defined parameters and properties, may be also representative for such a sampler for acquiring removable particulate contamination.

The typical measurement temperature at which the particulate contamination measurement apparatus or a sampler for acquiring removable particulate contamination is usable for various applications such as listed above may be for instance in a range from 10 to 50° C.

Although specific reference has been made above to polyurethane elastomer polymers, it is to be understood that the particulate contamination measurement apparatus or the sampler for acquiring removable particulate contamination according to the invention may comprise any type of a flexible material, such as polymer, which has the hardness and ultra-clean properties and which is manufactured in controlled conditions as described above. Therefore, the above defined parameters and properties with reference to the polyurethane elastomer 2 can be defined in same way also for other types of flexible materials, since the hardness, roughness, cleanliness, etc. requirements of the flexible material are characteristic to the application field where such apparatus or sampler is used (for example for EUV lithography). Similarly, the characteristics described above regarding the shape (credit card blank shaped carrier, roller, tape, etc) and components of the particulate contamination measurement apparatus (carrier 1, foil 4, layer 2, protecting foil, etc) or of the sampler for acquiring removable particulate contamination are also generally valid for any suitable flexible material and depend mainly on the application field where such apparatus or sampler is intended to be used.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion," respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The term "lens," where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. A particulate contamination measurement apparatus comprising:
   a layer of polyurethane elastomer having a measurement surface;
   a carrier configured to carry the layer of polyurethane elastomer,
   wherein the measurement surface of the layer of polyurethane elastomer is configured to:
      be pressed against a surface being measured; and
      be removed from the surface being measured with no residue being transferred from the layer of polyurethane elastomer to the surface being measured.

2. The particulate contamination measurement apparatus of claim 1, wherein the measurement surface of the layer of polyurethane elastomer is ultra-clean.

3. The particulate contamination measurement apparatus of claim 1, wherein the layer of polyurethane elastomer has a hardness value below 80 on a Shore A hardness measurement scale.

4. The particulate contamination measurement apparatus of claim 1, wherein the layer of polyurethane elastomer has a hardness value greater than 20 on a Shore OO hardness measurement scale or greater than 20 on a Shore A hardness measurement scale.

5. The particulate contamination measurement apparatus of claim 1, wherein the layer of polyurethane elastomer has a hardness value in a range from 38 to 75 on a Shore A hardness measurement scale.

6. The particulate contamination measurement apparatus of claim 1, wherein the measurement surface of the layer of polyurethane elastomer has an average roughness (Ra) equal to or less than 1 micron.

7. The particulate contamination measurement apparatus of claim 1, wherein:
   the carrier, comprises a hole; and
   the measurement surface of the layer of polyurethane elastomer is configured to be accessible through the hole.

8. The particulate contamination measurement apparatus of claim 7, wherein the carrier is flexible.

9. The particulate contamination measurement apparatus of claim 1, wherein the carrier has a shape and size of a credit card blank.

10. The particulate contamination measurement apparatus of claim 7, further comprising a flexible sheet material on an opposite side of the layer of polyurethane elastomer from the hole.

11. The particulate contamination measurement apparatus of claim 1, wherein:
the carrier comprises a probe; and
the layer of polyurethane elastomer is provided on an end of the probe.

12. A particulate contamination measurement method, the method comprising:
carrying a polyurethane elastomer on a carrier;
pressing a measurement surface of the polyurethane elastomer against a surface being measured;
removing the polyurethane elastomer from the surface with no residue transferred from the polyurethane elastomer to the surface being measured; and
detecting, using an optical apparatus, particles that are removed by the polyurethane elastomer from the surface and that are attached to the polyurethane elastomer.

13. The method of claim 12, further comprising using a hardness value below 80 on a Shore A hardness measurement scale for a hardness property of the polyurethane elastomer.

14. The method of claim 12, further comprising using a hardness value greater than 20 on a Shore OO hardness measurement scale or greater than 20 on a Shore A hardness measurement scale for a hardness property of the polyurethane elastomer.

15. The method of claim 12, further comprising using an average roughness (Ra) equal to or less than 1 micron for a roughness property of the polyurethane elastomer.

16. The method of claim 12, further comprising:
using a substrate that is provided with a hole for the carrier; and
accessing the measurement surface of the polyurethane elastomer through the hole.

17. The method of claim 12, further comprising using a flexible substrate for the carrier.

18. The method of claim 12, further comprising:
using a probe for the carrier; and
providing the polyurethane elastomer on an end of the probe.

19. The particulate contamination measurement apparatus of claim 1, wherein the layer of polyurethane elastomer is configured to be self-adhesive to the carrier.

* * * * *

UNITED STATES PATENT AND TRADEMARK OFFICE
CERTIFICATE OF CORRECTION

PATENT NO. : 9,638,643 B2  
APPLICATION NO. : 14/389075  
DATED : May 2, 2017  
INVENTOR(S) : De Jong et al.

Page 1 of 1

It is certified that error appears in the above-identified patent and that said Letters Patent is hereby corrected as shown below:

On the Title Page

(73) Assignee section, please add --TNO, Delft (NL)--.

Signed and Sealed this  
Eighth Day of May, 2018

Andrei Iancu  
*Director of the United States Patent and Trademark Office*